US008669236B2

(12) United States Patent
Elmaleh et al.

(10) Patent No.: US 8,669,236 B2
(45) Date of Patent: Mar. 11, 2014

(54) BIOTINYLATED COMPOSITIONS

(75) Inventors: David R. Elmaleh, Newton, MA (US); Bruce R. Zetter, Wayland, MA (US); Earl Weinstein, Beverly Hills, CA (US); Jacqueline Banyard Bhisitkul, Southborough, MA (US)

(73) Assignees: The General Hospital Corporation, Charlestown, MA (US); Children's Medical Center Corporation, Boston, MA (US)

( * ) Notice: Subject to any disclaimer, the term of this patent is extended or adjusted under 35 U.S.C. 154(b) by 327 days.

(21) Appl. No.: 11/914,332

(22) PCT Filed: May 12, 2006

(86) PCT No.: PCT/US2006/018639
§ 371 (c)(1),
(2), (4) Date: Oct. 28, 2008

(87) PCT Pub. No.: WO2006/124726
PCT Pub. Date: Nov. 23, 2006

(65) Prior Publication Data
US 2009/0220433 A1    Sep. 3, 2009

Related U.S. Application Data

(60) Provisional application No. 60/680,133, filed on May 12, 2005.

(51) Int. Cl.
C12N 15/11 (2006.01)

(52) U.S. Cl.
USPC ...................................... 514/44 A

(58) Field of Classification Search
USPC ............ 435/6, 91.1, 91.31, 455; 514/1, 2, 44, 514/44 A; 536/23.1, 24.5, 26.6, 106, 127
See application file for complete search history.

(56) References Cited

U.S. PATENT DOCUMENTS

| | | | |
|---|---|---|---|
| 3,420,788 A | 1/1969 | Solms | |
| 3,426,011 A | 2/1969 | Parmerter | |
| 3,453,257 A | 7/1969 | Parmerter | |
| 3,453,259 A | 7/1969 | Parmerter | |
| 3,459,731 A | 8/1969 | Gramera et al. | |
| 4,235,871 A | 11/1980 | Papahadjopoulos et al. | |
| 4,605,735 A | 8/1986 | Miyoshi et al. | |
| 4,615,879 A | 10/1986 | Runge et al. | |
| 4,639,365 A | 1/1987 | Sherry | |
| 4,675,173 A | 6/1987 | Widder | |
| 4,687,658 A | 8/1987 | Quay | |
| 4,687,659 A | 8/1987 | Quay | |
| 4,709,037 A | 11/1987 | Sigler | |
| 4,711,955 A | 12/1987 | Ward et al. | |
| 4,737,323 A | 4/1988 | Martin et al. | |
| 4,751,313 A | 6/1988 | Levenson et al. | |
| 4,794,082 A | 12/1988 | Sigler | |
| 4,798,795 A | 1/1989 | Sigler | |
| 4,908,453 A | 3/1990 | Cocuzza | |
| 4,925,652 A | 5/1990 | Gries et al. | |
| 5,128,476 A | 7/1992 | Zhang et al. | |
| 5,134,127 A | 7/1992 | Stella et al. | |
| 5,180,828 A | 1/1993 | Ghazarossian et al. | |
| 5,252,743 A | 10/1993 | Barrett et al. | |
| 5,716,594 A | 2/1998 | Elmaleh et al. | |
| 6,120,751 A | 9/2000 | Unger | |
| 6,506,559 B1 | 1/2003 | Fire et al. | |
| RE38,442 E * | 2/2004 | Zhang et al. ...................... 435/5 |
| 6,770,729 B2 | 8/2004 | Van Antwerp | |
| 8,202,544 B2 * | 6/2012 | Papineni et al. ............. 424/499 |
| 2003/0091640 A1 | 5/2003 | Ramanathan et al. | |
| 2005/0059028 A1 * | 3/2005 | Nguyen et al. ..................... 435/6 |
| 2005/0136008 A1 | 6/2005 | Elmaleh et al. | |
| 2005/0260757 A1 * | 11/2005 | Gebeyehu et al. ............. 435/458 |
| 2006/0223770 A1 * | 10/2006 | Fougerolles et al. ........... 514/44 |
| 2006/0257949 A1 * | 11/2006 | Ross et al. ................... 435/7.23 |
| 2009/0068106 A1 * | 3/2009 | Corti et al. .................... 424/9.1 |
| 2009/0104195 A1 * | 4/2009 | Herman ..................... 424/136.1 |
| 2011/0054160 A1 * | 3/2011 | Manoharan et al. ......... 536/24.5 |

FOREIGN PATENT DOCUMENTS

| | | |
|---|---|---|
| CA | 1 218 597 | 3/1987 |
| CA | 1 253 514 | 5/1989 |
| CA | 1 341 176 | 1/2001 |
| DE | 3401052 | 7/1984 |
| DE | 3443252 | 5/1986 |
| DE | 3629194 A1 | 3/1987 |
| EP | 136812 A2 | 4/1985 |
| EP | 165728 A1 | 12/1985 |
| EP | 185899 A2 | 7/1986 |
| EP | 186947 A1 | 7/1986 |
| EP | 230893 A2 | 8/1987 |
| EP | 232751 A1 | 8/1987 |
| EP | 292689 A2 | 11/1988 |
| WO | WO-85/02772 A1 | 7/1985 |
| WO | WO-85/04330 A1 | 10/1985 |

(Continued)

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Jang, H.-H. et al., Expert Rev. Medical Devices, vol. 1, No. 1, pp. 127-138 (2004).*
Bass, B. L., "The Short Answer", Nature, 411:428-429 (London, England, 2001).
Billy, E. et al., "Specific interference with gene expression induced by long, double-stranded RNA in mouse embryonal teratocarcinoma cell lines," Proc. Natl. Acad. Sci., 98(25):14428-14433 (United States, Dec. 4, 2001).
Boutla, A. et al., "Short 5'-phosphorylated double-stranded RNAs induce RNA interference in Drosophila," Curr. Biol., 11:1776-1780 (Elsevier Science Ltd., Nov. 13, 2001).
Brasch, R.C., "Work in Progress: Methods of Contrast Enhancement for NMR Imaging and Potential Applications. A subject review.", Radiology, 147(3):781-7888 (United States, Jun. 1983).

(Continued)

Primary Examiner — Brian Whiteman
(74) Attorney, Agent, or Firm — Foley Hoag LLP

(57) ABSTRACT

Novel biotinylated composition comprising a nucleic acid, e.g. siRNA, that are useful for targeting therapeutic and imaging agents to sites of infection and tumors are disclosed.

12 Claims, 7 Drawing Sheets

(56) References Cited

FOREIGN PATENT DOCUMENTS

| WO | WO-85/05554 A1 | 12/1985 |
|---|---|---|
| WO | WO-85/05638 A1 | 12/1985 |
| WO | WO-86/01112 A1 | 2/1986 |
| WO | WO-87/01594 A1 | 3/1987 |
| WO | WO-87/02893 A1 | 5/1987 |
| WO | WO-88/00060 A1 | 1/1988 |
| WO | WO-89/00078 A1 | 1/1989 |
| WO | WO-89/00557 A1 | 1/1989 |
| WO | WO-89/06979 A1 | 8/1989 |
| WO | WO-96/14057 A1 | 5/1996 |
| WO | WO 2005037056 A2 * | 4/2005 |

OTHER PUBLICATIONS

Crawford, C. R. et al., "High Speed Reprojection and its Applications", Proc. SPIE—Int. Soc. Opt. Eng. Conf. Medical Imaging II, Newport Beach, Calif., 914(A):311-318 (United States, 1988).
Davidson, B.L. et al., "Molecular medicine for the brain: silencing of disease genes with RNA interference", Lancet, 3:145-149 (2004).
Dordunoo, S. K. et al., "Preformluation Studies on Solid Dispersions Containing Triamterene or Temazepam in Polyethylene Glycols or Gelucire 44/14 for Liquid Filling of Hard Gelatin Capsules." Drug Development and Industrial Pharmacy, 17(12):1685-1713 (United Kingdom, 1991).
Doyle, F. H. et al., "Relaxation Rate Enhancement Observed In Vivo by NMR Imaging", J. Comput. Assist. Tomogr., 5(2):295 (1981).
Elbashir, S. M. et al., "Analysis of gene function in somatic mammalian cells using small interfering RNAs," Methods, 26(2):199-213 (Feb. 2002).
Elbashir, S. M., et al. "Duplexes of 21-nucleotide RNAs mediate RNA interference in cultured mammalian cells," Nature, 411:494-498 (May 24, 2001).
Elbashir, S. M., et al. "RNA interference is mediated by 21- and 22-nucleotide RNAs," Genes & Dev. 15:188-200 (2001).
Elbashir, S. M., et al. "Functional anatomy of siRNAs for mediating efficient RNAi in Drosophila melanogaster embryo lysate," The EMBO Journal, 20(23):6877-6888 (2001).
Elmaleh, D.R. et al., "99mTc-labeled nucleotides as tumor-seeking radiodiagnostic agents", Proc. Natl. Acad. Sci., 81:918-921 (United States, 1984).
Filleur, S. et al., "SiRNA-mediated Inhibition of Vascular Endothelial Growth Factor Severely Limits Tumor Resistance to Antiangiogenic Thrombospondin-1 and Slows Tumor Vascularization and Growth", Cancer Res., 63:3919-3922 (Jul. 15, 2003).
Fire, A. et al., "Potent and specific genetic interference by double-stranded RNA in Caenorhabditis elegans", Nature, 391:806-811 (Macmillan Publishers Ltd., Feb. 19, 1998).
Grosshans, H. et al., "Micro-RNAs: small is plentiful", J. Cell Biol., 156(1):17-22 (Jan. 7, 2002).
Hammond, S. M. et al., "An RNA-directed nuclease mediates post-transcriptional gene silencing in Drosophila cells", Nature, 404:293-296 (London, England, 2000).
Harborth, J. et al., "Identification of essential genes in cultured mammalian cells using small interfering RNAs", J. Cell Sci., 114(24):4557-4565 (The Company of Biologists Ltd., 2001).
Hutvagner, G. et al., "A Cellular Function for the RNA-Interference Enzyme Dicer in the Maturation of the let-7 Small Temporal RNA", Science, 293:834-838 (Aug. 3, 2001).
Koutcher, J. A. et al., "Contrast Agents and Spectroscopic Probes in NMR", J. Nuclear Med., 25(4):506-13 (Boston, MA, Apr. 1984).
Krieg, A.M., "CPG Motifs in Bacterial DNA and Their Immune Effects", Annu. Rev. Immunol., 20:709-760 (Cambridge, MA, 2002).

Lauterbur, P. C. et al., "Augmentation of Tissue Water Proton Spin-Lattice Relaxation Rates by In Vivo Addition of Paramagnetic Ions", Frontiers of Biological Energetics, vol. 1, 1:752-759 (Academic Press, 1978).
Lauterbur, P. C., "Progress in n. m.r. zeugmatographic imaging", Phil. trans. R. Soc. Lond., 289:483-478 (Great Britain, 1980).
Layzer, J. M. et al., "In vivo activity of nuclease-resistant siRNAs," RNA 10:766-771 (Cold Spring Harbor Laboratory Press, 2004).
Lipardi, C. et al., "RNAi as Random Degradative PCR: siRNA Primers Convert mRNA into dsRNAs that Are Degraded to Generate New siRNAs", Cell, 107:297-307 (NIH, Bethesda, Maryland, Nov. 2, 2001).
Mendonça-Dias, M. H. et al., "Paramagnetic contrast agents in nuclear magnetic resonance medical imaging", Semin. Nucl. Med., 13(4):364-76 (SUNY, Stony Brook, New York, Oct. 1983).
Nykanen, A. et al., "ATP Requirements and Small Interfering RNA Structure in the RNA Interference Pathway", Cell, 107:309-321 (Nov. 2, 2001).
Paddison, P. J. et al., "Stable suppression of gene expression by RNAi in mammalian cells", Proc. Natl. Acad. Sci., 99(3):1443-1448 (USA, Feb. 5, 2002).
Parrish, S. et al., "Functional Anatomy of a dsRNA Trigger: Differential Requirement for the Two Trigger Strands in RNA Interference", Mol. Cell, 6:1077-1087 (USA, Nov. 2000).
Robertson, H. D. et al., "The regulation of the protein kinase PKR by RNA", Biochimie, 78:909-914 (USA, Dec. 4, 1996).
Runge, V. M. et al., "Paramagnetic Agents for Contrast-Enhanced NMR Imaging: A Review", AJR Am J Roentgenol., 141(6):1209-15 (USA, Dec. 1983).
Runge, V. M. et al. "Work in Progress: Potential Oral and Intravenous Paramagnetic NMR Contrast Agents," Radiology. 147(3):789-91 (Jun. 1983).
Sheen, P. C. et al., "Bioavailability of a poorly water-soluble drug from tablet and solid dispersion in humans", J. Pharm. Sci., 80(7):712-714 (USA, 1991).
Sijen, T. et al., "On the Role of RNA Amplification in dsRNA-Triggered Gene Silencing", Cell, 107:465-476 (Nov. 16, 2001).
Song, E. et al., "RNA Interference targeting Fas protects mice from fulminant hepatitis", Nature Med., 9(3):347-351 (USA, Mar. 2003).
Tolentino, M. J. et al., "Intravitreal Injection of Vascular Endothelial Growth Factor Small Interfering RNA Inhibits Growth and Leakage in a Nonhuman Primate, Laser-Induced Model of Choroidal Neovascularization", Retina, 24(1):132-138 (USA, 2004).
Van Uden, W. et al., "Cyclodextrins as a useful tool for bioconversions in plant cell biotechnology", Plant Cell Tiss. Org. Cult., 38:1-3-113 (Netherlands, 1994).
Weissleder, R. et al., "Dual-Contrast MR Imaging of Liver Cancer in Rats", AJR Am J Roentgenol., 150(3):561-6 (USA, Mar. 1988).
Weissleder, R. et al., "Pyogenic Liver Abscess: Contrast-Enhanced MR Imaging in Rats", AJR Am J Roentgenol., 150(1):115-20 (USA, Jan. 1988).
Wenz, G., "Cyclodextrins as Building Blocks for Supramolecular Structures and Functional Units", Agnew. Chem. Int. Ed. Engl., 33:803-822 (Germany, 1994).
Yang, D. et al., "Evidence that processed small dsRNAs may mediate sequence-specific mRNA degradation during RNAi in Drosophila embryos", Curr. Biol., 10(19):1191-1200 (Elsevier Science Ltd., Sep. 19, 2000).
Yang, S. et al., "Specific Double-Stranded RNA Interference in Undifferentiated Mouse Embryonic Stem Cells", Mol. & Cell. Biol., 21(22):7807-7816 (USA, Nov. 2001).
Zamore, P. D. et al., "RNAi: Double-Stranded RNA Directs the ATP-Dependent Cleavage of mRNA at 21 to 23 Nucleotide Intervals", Cell, 101:25-33 (USA, Mar. 31, 2000).

* cited by examiner

Formula 2

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 1
aannnnnnnn nnnnnnnnnn ntt                                              23

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```

```
gttggagctg ttggcgtag                                          19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagctgttgg cgtaggcaa                                          19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
gagcuguugg cgtaggcaa                                          19
```

BIOTINYLATED COMPOSITIONS

CROSS-REFERENCE TO RELATED APPLICATION

This application is a National Stage of International Application No. PCT/US2006/018639, filed May 12, 2006, which claims the benefit of U.S. Provisional Patent Application Ser. No. 60/680,133, filed May 12, 2005, both of which are hereby incorporated by reference in their entirety.

BACKGROUND OF THE INVENTION

RNA interference or "RNAi" is a term coined by Fire and co-workers to describe the observation that certain double-stranded RNAs (dsRNAs) blocked gene expression when they were introduced into worms. Introduction of dsRNA into a cell leads to the sequence-specific destruction of endogenous RNAs that have sequences that are complementary to the dsRNA. During RNAi, long dsRNA molecules are processed into 19- to 23-nt RNAs known as short-interfering RNAs (siRNAs) that serve as guides for enzymatic cleavage of complementary RNAs. In addition, siRNAs can function as primers for an RNA-dependent RNA polymerase that synthesizes additional dsRNA, which in turn is processed into siRNAs, amplifying the effects of the original siRNAs. In mammalian cells, dsRNA is processed into siRNAs, but RNAi with dsRNA has not been successful in most cell types because of nonspecific responses elicited by dsRNA molecules longer than about 30 nt. However, Tuschl and coworkers observed that transfection of synthetic 21-nt siRNA duplexes into mammalian cells effectively inhibited endogenous genes in a sequence-specific manner. These siRNA duplexes are too short to trigger the nonspecific dsRNA responses, but they still cause destruction of complementary RNA sequences.

One particularly problematic aspect of administering any pharmaceutical compound is the delivery of the compound to the desired tissue in the patient. In particular, antisense and siRNA therapeutics to date have been hindered by poor intracellular uptake, limited blood stability and non-specific immune stimulation. For siRNA therapeutics for cancer, the pharmacological hurdles are severe. Local aqueous siRNA activity has been observed for several tissues, but is lacking in tumors, and systemic exposure can induce non-specific responses, as found for CpG DNA oligonucleotides. Although the potency and selectivity of siRNA inhibitors of gene expression promises to enable improved targeted cancer therapeutics, the means for systemic administration and targeted distribution to affected cells and tissues are needed.

Two basic approaches for targeting tumors with the avidin-biotin system have been used in patients and animals. In the first method, avidin (or streptavidin)-conjugated antibodies are injected and days later when antibody-tumor binding is maximized, a radioactive biotin derivative is injected to localize the tumor. Unfortunately, incomplete clearance of unbound antibody from the blood can obscure visualization of the target site. In the second method, blood background is reduced by injecting biotinylated antibodies followed three days later by cold avidin. The resultant circulating biotinylated antibody-avidin complexes are sequestered from the blood by the liver. Radioactive biotin is then injected which binds to the antibody-biotin-avidin complexes already localized in the tumor. However, by employing "pretargeting" steps, both approaches for targeting tumors require that a subject be available to undergo multiple procedures over the course of a few days.

SUMMARY OF THE INVENTION

The invention relates generally to novel biotinylated compositions comprising a nucleic acid based therapeutic agent, in particular, an siRNA or other nucleic acid, nucleotide, oligonucleotide or nucleotide-associated protein. We have shown that biotinylated siRNAs are taken up by tumor cells in the absence of delivery reagent, and act functionally to silence gene expression. Biotinylation of siRNA allows for more effective intracellular delivery of the siRNA molecule, e.g. for more effective silencing. Such compositions are useful in the delivery or targeting of therapeutic or diagnostic agents, for example delivery or targeting of iRNA and antisense agents to a tumor cell. In certain embodiments, the compositions of the invention comprise a polymer core to which several biotin moieties are conjugated and to which at least nucleic acid based therapeutic agent is conjugated. In one embodiment, four biotin moieties are conjugated to the 3' and 5' ends of the sense and antisense strands of a double-stranded nucleic acid. In other embodiments, the biotin moieties are conjugated to a polymeric core by a tether comprising an amide bond on several sides and to at least one nucleic acid based therapeutic agent. In certain embodiments, the biotinylated compositions may further comprise at least one additional therapeutic agent, at least one diagnostic agent, and/or at least one targeting moiety that may be conjugated to the composition as well. In another aspect, the invention relates to a method of treating a subject using the biotinylated compositions. The subject may have e.g., cancer or an infection. In still yet another aspect, the invention features methods of delivering the biotinylated compositions to a cell or tissue. The methods may include contacting a biotinylated composition described herein with the cell and allowing the cell to take up the composition. In yet another aspect of the invention, the biotinylated compositions may be used in a method of acquiring a magnetic resonance, radionuclide or fluorescent image. Provided also are kits that include at least one biotinylated composition described herein and instructions for using the composition.

DETAILED DESCRIPTION OF THE INVENTION

Definitions

Figure 1:
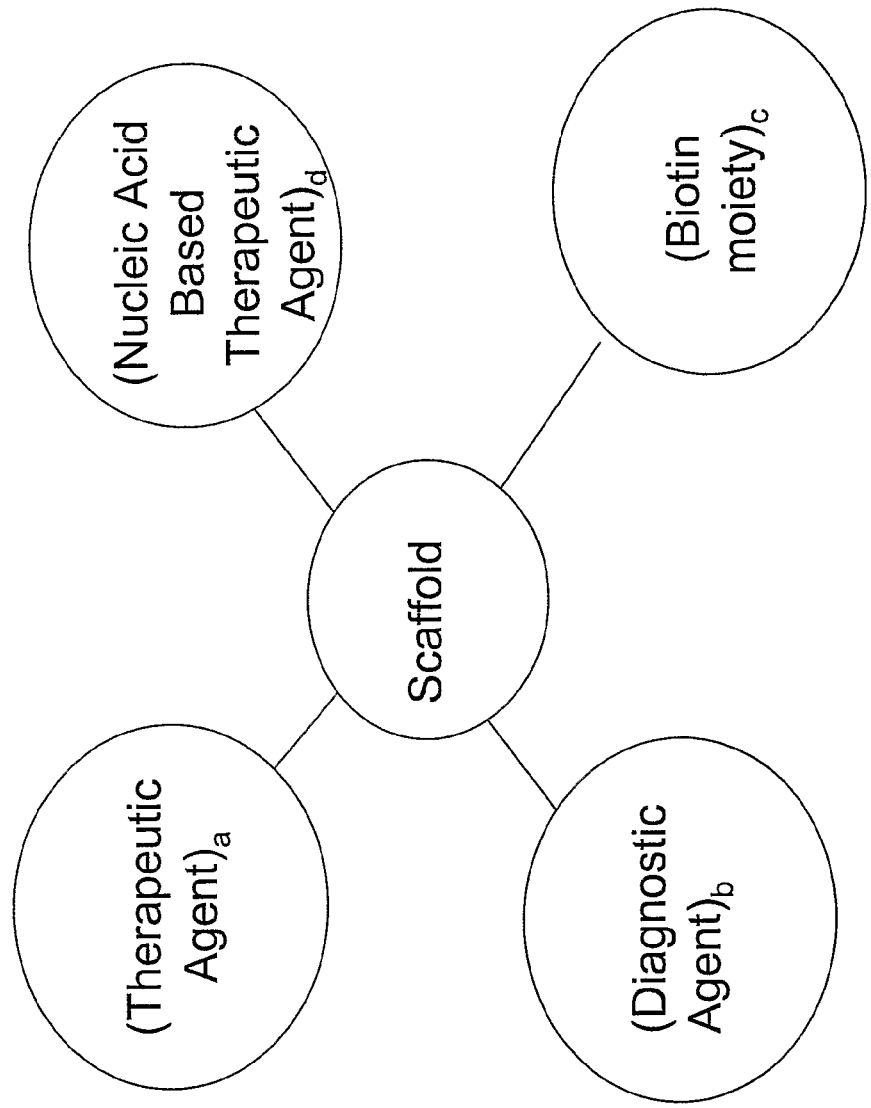
FIG. 1 depicts a general schematic of the biotinylated compositions described herein (Formula 1). The subscript indicates how many of each substituent there may be: a can be 0 or at least 1, b can be 0 or at least 1, c is at least 1 and d is at least one.
Figure 2:
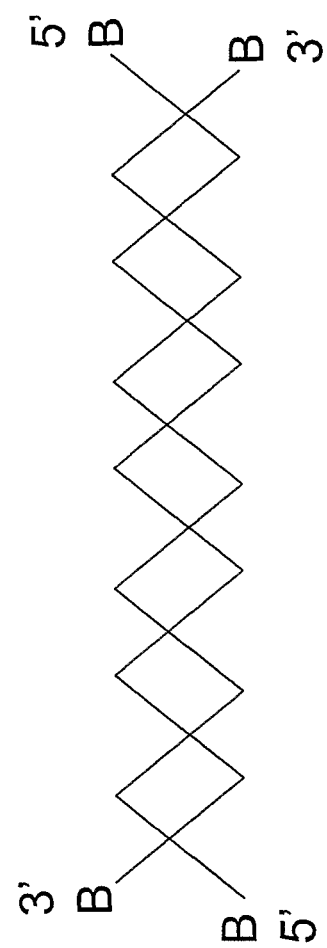
FIG. 2 depicts a schematic representation of the double-stranded oligonucleotide tetrabiotin compositions described herein (Formula 2), wherein "B" shows a potential site for conjugation of a biotin moiety at each of the 5' and 3' sites. At least one such site in the compositions of the invention is conjugated to a biotin moiety.
Figure 3:
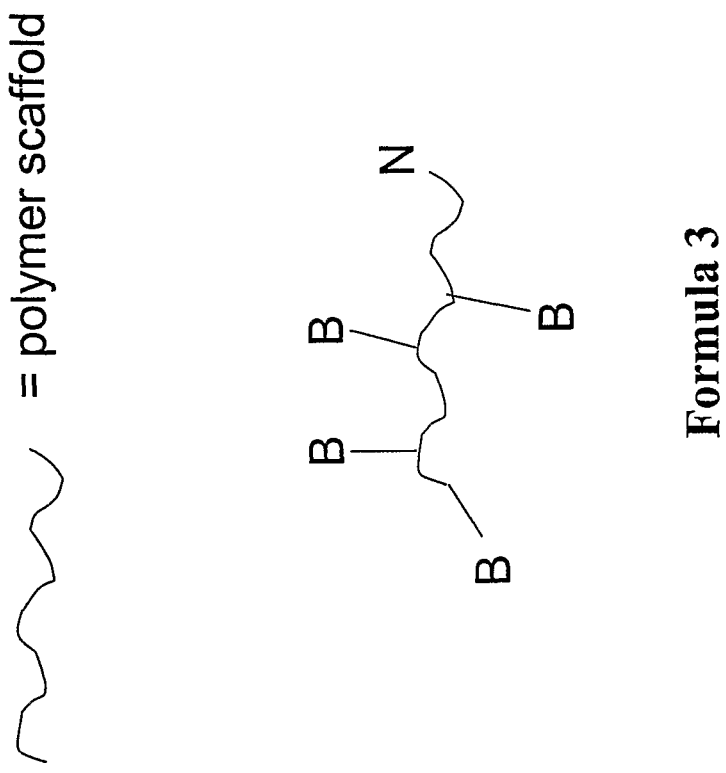
FIG. 3 depicts a general schematic of the biotin-loaded polymer compositions described herein. The polymer may contain any number of biotin moieties ("B"). The more biotin moieties contained, the higher the internalization probability. N represents a nucleic acid based therapeutic agent.
Figure 4:
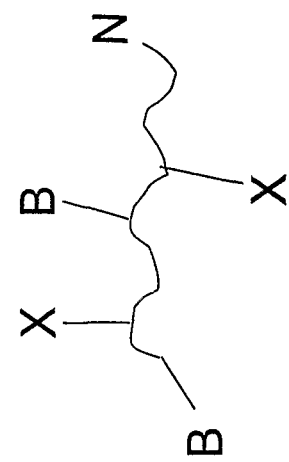
FIG. 4 depicts several nonlimiting examples of biotinylated polymer compositions conjugated to at least one nucleic acid based therapeutic agent ("N") and at least one other component ("X", e.g. another therapeutic agent, a diagnostic agent and/or a delivery agent).
Figure 4:
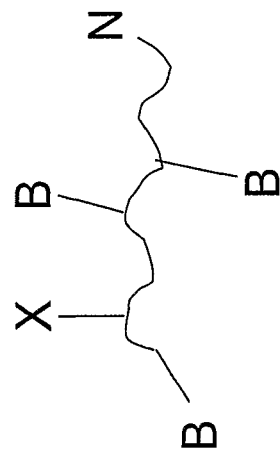
Figure 4:
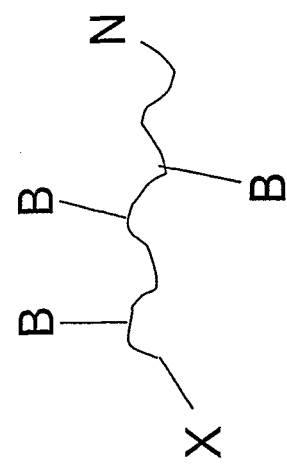

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

"Antisense" nucleic acids refer to nucleic acids that specifically hybridize (e.g., bind) with a nucleic acid, e.g., cellular mRNA and/or genomic DNA, under cellular conditions so as to inhibit expression (e.g., by inhibiting transcription and/or translation). The binding may be by conventional base pair complementarity or, for example, in the case of binding to DNA duplexes, through specific interactions in the major groove of the double helix.

"Biological sample" or "sample", refers to a sample obtained from an organism or from components (e.g., cells) of an organism. The sample may be of any biological tissue, component or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Samples may also comprise cell extracts and purified components, such as proteins, nucleic acids, and the like, from such cell extracts.

The terms "comprise" and "comprising" are used in the inclusive, open sense, meaning that additional elements may be included.

"Conjugated" shall mean ionically or, preferably, covalently attached (e.g., via a crosslinking agent).

A "scaffold" refers to any molecule, e.g. a polymer, that can serve as a molecular core to which the various agents (biotin moiety, nucleic acid based agent, diagnostic agent, etc.) of the invention may be conjugated to form the biotinylated compositions of the invention.

A "diagnostic agent" shall mean a composition capable of generating a detectable image upon binding with a target and shall include fluorophores, chromophores, radionuclides (e.g., In-111, Tc-99m, I-123, I-125 F-18, Ga-67, Ga-68, and for Positron Emission Tomography (PET) and Single Photon Emission Tomography (SPECT), unpair spin atoms and free radicals (e.g., Fe, lanthanides, and Gd) and contrast agents (e.g., chelated (DTPA) manganese) for Magnetic Resonance Imaging (MRI).

The language "effective amount" of a targeted therapeutic agent or imaging agent refers to that amount necessary or sufficient to eliminate, reduce, or maintain (e.g., prevent the spread of) an infection, tumor, or other target. The effective amount can vary depending on such factors as the disease or condition being treated, the particular targeted constructs being administered, the size of the subject, or the severity of the disease or condition. One of ordinary skill in the art can empirically determine the effective amount of a particular compound without necessitating undue experimentation.

"Gene" or "recombinant gene" refer to a nucleic acid molecule comprising an open reading frame and including at least one exon and (optionally) an intron sequence. "Intron" refers to a DNA sequence present in a given gene which is spliced out during mRNA maturation.

The term "gene silencing" means interruption or suppression of the expression of a gene at transcriptional or translational levels The term "including" is used to mean "including but not limited to". "Including" and "including but not limited to" are used interchangeably.

A "nucleic acid based therapeutic agent" refers to a therapeutic agent that is a nucleic acid, nucleotide, oligonucleotide or nucleotide-associated protein.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides. Exemplary nucleic acids for use in the subject invention include antisense, siRNA, mRNA, cDNA and the like.

A "nucleotide-associated protein: refers to any protein or polypeptide having the ability to bind a nucleotide and act on it, e.g., to regulate splicing, transcription, etc.

As used herein, the term "oligonucleotide" refers to a nucleic acid molecule (RNA or DNA) preferably of length less than 100, 200, 300, or 400 nucleotides.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

A "patient" or "subject" or "host" refers to either a human or non-human animal.

"Pharmaceutically-acceptable salts" refers to the relatively non-toxic, inorganic and organic acid addition salts of compounds.

"Pharmaceutically acceptable carrier" refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

"siRNA" as used herein, a double stranded RNA or single stranded RNA, that can enter a RISC(RNAi-induced silencing complex) and is sufficiently short that it does not induce a deleterious interferon response in a human cell, e.g., it has a duplexed region of less than 60 but preferably less than 50, 40, or 30 nucleotide pairs. The siRNA or a cleavage product thereof can down regulate a target gene, e.g., by inducing RNAi with respect to a target RNA, preferably an endogenous or pathogen target RNA.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

A "target" shall mean an in vivo site to which biotin compounds bind. A preferred target is a tumor (e.g., tumors of the brain, lung (small cell and non-small cell), ovary, prostate, breast and colon as well as other carcinomas and sarcomas). Another preferred target is a site of infection (e.g. by bacteria, viruses (e.g. HIV, herpes, hepatitis) and pathogenic fungi (*Candida* sp.). Particularly preferred target infectious organisms are those that are drug resistant (e.g. *Enterobacteriaceae, Enterococcus, Haemophilus influenza, Mycobacterium tuberculosis, Neisseria,* gonorrhoeae, *Plasmodium falciparum, Pseudomonas aeruginosa, Shigella dysenteriae, Staphylococcus aureus, Streptococcus pneumoniae*). The localization of biotin at a site of infection, may be related to that fact that it is an essential nutrient of many bacteria, viruses and fungi.

The term "targeting moiety" refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins can serve as targeting moieties.

"Therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a at a reasonable benefit/risk ratio applicable to such treatment.

The term "treating" is art-recognized and refers to curing and preventing a condition or disease, as well as ameliorating at least one symptom of any condition or disease or preventing a condition or disease from worsening.

Compositions of the Invention

The biotinylated compositions of the invention comprise a scaffold. The compound comprising the scaffold may be, for example, a naturally occurring compound such as a nucleic acid, a compound derived from a natural compound, such as a nucleic acid analog or a synthesized compound, e.g. a synthetic polymer. In certain embodiments, at least one and preferably at least two biotin moieties are conjugated to the scaffold. The biotin moieties may serve to direct the therapeutic, drug delivery agent or diagnostic agent to a desired site with higher specificity. In certain embodiments, the biotin moieties are conjugated to the scaffold by a tether comprising at least one covalent bond. In one embodiment, the tether comprises at least one amide bond, and in other embodiments, the tether is an alkyl group that contains at least two amide bond linkages. In certain embodiments, the scaffold is substituted with at least one biotin moiety and at least one therapeutic agent. In another embodiment, the scaffold is substituted with at least one biotin moiety, at least one detectable moiety and at least one therapeutic agent. In other embodiments, the scaffold is substituted with at least one biotin moiety, at least one therapeutic agent and at least one targeting moiety and/or at least one diagnostic agent.

Exemplary compositions of the invention are depicted in FIGS. 1 through 4.

The term "biotin moiety" encompasses biotin (hexahydro-2-oxo-1H-thieno[3,4-d]imidazole-4-pentanoic acid); a 244 dalton vitamin, analogs and derivatives thereof, as well as compounds comprising multiple biotin moieties. Exemplary biotin analogs that may be used in the compositions of the invention are described in U.S. Pat. No. 5,716,594 by Elmaleh, et al, which patent hereby incorporated by reference in its entirety and exemplary compounds comprising multiple biotin moieties (e.g., "polybiotin compounds") that may be used in the compositions of the invention are described in U.S. Ser. No. 10/956,687, "Polybiotin Compounds for Magnetic Resonance Imaging and Drug Discovery" filed Oct. 1, 2004 by Elmaleh, et al., which application is hereby incorporated by reference in its entirety. Patents and literature are replete with other exemplary biotin moieties including various spacers, linking groups and the like, for use in the present applications. Nonlimiting examples can be found in M. D. Savage, et al. (1992), Pierce Chemical Co., Avidin-Biotin Chemistry: A Handbook; DE 3629194, U.S. Pat. Nos. 5,180, 828, 4,709,037 and 5,252,743, 4,798,795, 4,794,082, WO 85/05638 all incorporated herein by reference.

Methods of conjugating biotin moieties to other chemical entities (i.e., methods of biotinylation) are well-known in the art. For example, a biotin moiety (which can be any desired biotin compound optionally with spacer arm and/or leaving group) such as N-hydroxysuccinimide-biotin (NHS-biotin) can be reacted with the desired biomolecule, e.g., the scaffold, in a solvent and in the presence of a buffer. The NHS functions as a leaving group to provide the so-formed biotinylated scaffold. This can be purified using standard methodology, for example, subjecting the biotinylated scaffold to purification on a Sephadex.™ chromatography column to remove free biotin, NHS-biotin and other low molecular weight solutes. Many methods for conjugating biotin moieties to oligonucleotides have been described in the art as well. See, for example, U.S. Pat. Nos. 5,128,476, 4,605,735, 4,751,313, 4,711,955, and 4,908,453. A variety of polymers may be used as scaffolds in the subject biotinylated compositions. Both non-biodegradable and biodegradable polymers may be used. As discussed below, the choice of polymer will depend in part on a variety of physical and chemical characteristics of such polymer and the use to which such polymer may be put. Polymers used as scaffolds may be, for example, natural, synthetic, modified natural, etc.

Representative natural polymers include proteins, such as zein, modified zein, casein, gelatin, gluten, serum albumin, or collagen, and polysaccharides, such as cellulose, dextrans, hyaluronic acid, and polymers of alginic acid.

Representative synthetic polymers include polyphosphazines, poly(vinyl alcohols), polyamides, polycarbonates, polyalkylenes, polyacrylamides, polyanhydrides, poly(phosphoesters), polyalkylene glycols, polyalkylene oxides, polyalkylene terephthalates, polyvinyl ethers, polyvinyl esters, polyvinyl halides, polyvinylpyrrolidone (PVP), polyglycolides, polysiloxanes, polyphosphates and polyurethanes.

Synthetically modified natural polymers include alkyl celluloses, hydroxyalkyl celluloses, cellulose ethers, cellulose esters, and nitrocelluloses. Other like polymers of interest include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

Examples of suitable polymers for use as scaffolds include, but are not limited to, polypeptides, polystyrene, polymethylmethacrylate, polyethylene glycol, polypropylene, polycarbonate, polyethylene, polyurethane, polypropylene glycol, expanded polytetrafluoroethylenes, fluorinated ethylene propylene, polyvinylalcohol, polycarbonate, polylactides, polyglycolids, polycaprolactides, polyarylates, polyanhydrides, and polyphosphoesters. In certain embodiments the polymer is polylysine. In certain embodiments, the polymer is biodegradable. Exemplary biodegradable polymers include, but are not limited to, polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Hydrophilic polymers suitable for use in the present invention are those which are readily water-soluble, can be covalently conjugated to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

All of the subject polymers may be provided as copolymers or terpolymers. These polymers may be obtained from chemical suppliers or else synthesized from monomers obtained from these suppliers using standard techniques.

In addition to the listing of polymers above, polymers having phosphorus linkages may be used in the subject invention. Exemplary phosphorus linkages in such polymers include, without limitation, phosphonamidite, phosphoramidite, phosphorodiamidate, phosphomonoester, phosphodiester, phosphotriester, phosphonate, phosphonate ester, phosphorothioate, thiophosphate ester, phosphinate or phosphite. Certain of such polymers may be biodegradable, biocompatible or both.

To allow coupling of siRNAs, biotin, and/or linker molecules, the surface chemical groups of a polymer can be derivatized with carboxyl (COOH), amino ($NH_2$), hydroxyl (OH), hydrazide ($NHNH_2$), amide ($CONH_2$), chloromethyl ($CH_3Cl$), and aldehyde (COH) groups. Such strategies for derivatizing and modifying various chemical groups (such as surface hydroxyl or amino groups) to allow coupling of lipids, carbohydrates, peptides, peptidomimetics, peptide-nucleic acids (PNAs), proteins, small molecules, natural products and oligonucleotides to a surface are well-known in the art.

For example, polymers can be modified by increasing the number of carboxylic groups accessible during biodegradation, or on the polymer surface. The polymers can also be modified by binding amino groups to the polymer. The polymers can also be modified using any of a number of different coupling chemistries that covalently attach ligand molecules to the surface-exposed molecules of the particles. Certain embodiments of the invention include polymers that have been carboxyl- and amino-modified. Covalent coupling via such moieties creates a high stability linkage between the polymer and molecule.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9-10 and normally requires at least 24 hrs. The resulting ligand-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex. By using either of these protocols it is possible to "activate" almost all polymers containing either hydroxyl or carboxyl groups in a suitable solvent system that will not dissolve the polymer matrix.

To create an amino-modified polymer, the addition of glutaraldehyde creates an aldehyde-activated surface, which can be attached to a molecule with a free amine. Amino groups on polymers may react with the bis-aldehyde molecule glutaraldehyde to form derivatives able to cross-link with aminogroups. The reaction mechanism for this modification can proceed by different ways. The more simple of these is the formation of a Schiff base linkage between one of the aldehyde ends and amines on the polymer to leave the other aldehyde terminal free to conjugate with another molecule. Schiff base interactions between aldehydes and amines typically are not stable enough to form irreversible linkages, and have to be reduced with suitable reductants. Amino modifying a polymer in this fashion results in a free binding moiety 11-12 carbon atoms away from the polymer, while carbodiimide results in 2-3 carbon linker. Additional linkers may be added to such moieties in order to space the siRNA or biotin from the polymeric scaffold, to provide flexibility, or to provide a particular orientation.

Another useful coupling procedure for attaching ligands with free hydroxyl and carboxyl groups to particles involves the use of the cross-linking agent, divinylsulfone. This method would be useful for attaching sugars or other hydroxylic molecules with bioadhesive properties to hydroxylic matrices. Briefly, the activation involves the reaction of divinylsulfone to the hydroxyl groups of a particle, forming the vinylsulfonyl ethyl ether of the particle. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of ligands and polymers with double bonds, including the use of UV crosslinking, may be used for attachment of molecules to the particles described herein.

Linkers (also known as "linker molecules" or "cross-linkers" or "spacers") may be used to conjugate the polymeric scaffold and a biotin molecule or siRNA. The majority of known cross-linkers react with amine, carboxyl, and sulfhydryl groups. Linker molecules may be responsible for different properties of the composition. The length of the linker should be considered in light of molecular flexibility during the conjugation step, and the availability of the conjugated molecule for its target. Longer linkers may thus improve the biological activity of the compositions of the present invention, as well as the ease of preparation of them. The geometry of the linker may be used to orient a molecule for optimal reaction with a target. A linker with flexible geometry may allow the entire biotinylated composition to conformationally adapt as it binds a target sequence. The nature of the linker may be altered for other various purposes. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many pre-made linkers for use in conjugating molecules are commercially available from vendors such as Pierce Chemical Co., Roche Molecular Biochemicals, United States Biological. Exemplary linker molecules for use in the compositions of the present invention include, but are not limited to: aminocaproic acid (ACA); polyglycine, and any other amino acid polymer, polymers such as polyethylene glycol (PEG), polymethyl methacrylate (PMMA), polypropylene glycol (PPG); homobifunctional reagents such as APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS; heterobifunctional reagents such as ABH, AEDP, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, MBuS, M2C2H, MPBH, MSA, NHS-ASA, PDPH, PMPI, SADP, SAED. SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS. Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS; and trifunctional linkers such as Sulfo-SBED, THPP β-[Tris(hydroxymethyl) phosphino] propionic acid (betaine) Any linkers contemplated for use include, but are not limited to, any molecule that does not contain a functionality incompatible with biotinylation or linking the siRNA to the scaffold.

Branched linkers may be prepared or used so that multiple moieties per linker are able to react with a polymeric scaffold. Such multiply reactive linkers allow the creation of multimeric binding sites.

In certain embodiments of the present invention, the linker may be a macromolecular polymer. Any of the above-mentioned polymers may comprise the macromolecular polymer. In certain embodiments, such macromolecular polymers may be comprised entirely of one type of polymeric molecule. In other embodiments, the macromolecular polymers may be comprised of more than one type of polymeric molecule. The macromolecular polymers may exist in many possible structures, for example, linear, comb-branched, dendrigraft, dendrimer, or a linear dendron architectural copolymer. For example, PEG and PPG may be used to create a variety of bi- and multivalent linkers. Methods of synthesizing, activating, and modifying branched PEG/PPG polymers and PEG/PPG block co-polymers are well-known in the art. PEG is hydrophilic, while PPG is hydrophobic. For instance, a linker could be synthesized with a PPG core and PEG branches.

Nucleic acid based therapeutic agents that may be used in the compositions of the invention include, but are not limited to, nucleic acids, nucleotides, oligonucleotides and nucleotide-associated proteins.

In certain embodiments, the nucleic acid based therapeutic agent is siRNA. Each strand of an sRNA agent can be equal to or less than 30, 25, 24, 23, 22, 21, or 20 nucleotides in length. The strand is preferably at least 19 nucleotides in length. For example, each strand can be between 21 and 25 nucleotides in length. Preferred sRNA agents have a duplex region of 17, 18, 19, 29, 21, 22, 23, 24, or 25 nucleotide pairs, and one or more overhangs, preferably one or two 3' overhangs, of 2-3 nucleotides.

The most efficient silencing is obtained with siRNA duplexes composed of 21-nt sense and 21-nt antisense strands, paired in a manner to have a 19-nucleotide duplex region and a 2-nt 3' overhang, (of preferably either UU or dTdT) at each 3' terminus. Symmetric 3'-overhangs ensure that the sequence-specific endonuclease complexes (siRNPs) are formed with approximately equal ratios of sense and antisense target RNA cleaving siRNPs. The 3'-overhang in the sense strand provides no contribution to recognition as it is believed the antisense siRNA strand guides target recognition. Therefore, the UU or dTdT 3'-overhang of the antisense sequences is complementary to the target mRNA but the symmetrical UU or dTdT 3'-overhang of the sense siRNA oligo does not need to correspond to the mRNA. The use of deoxythymidines in both 3'-overhangs may increase nuclease resistance, although siRNA duplexes with either UU or dTdT overhangs work equally well. 2'-Deoxynucleotides in the 3' overhangs are as efficient as ribonucleotides, but are often cheaper to synthesize.

The targeted region in the mRNA, and hence the sequence in the siRNA duplex, are chosen using the following guidelines. The open reading frame (ORF) region from the cDNA sequence is recommended for targeting, preferably at least 50 to 100 nucleotides downstream of the start codon, most preferably at least 75-100. Both the 5' and 3' untranslated regions (UTRs) and regions near the start codon are not recommended for targeting as these may be richer in regulatory protein binding sites. UTR-binding proteins and/or translation initiation complexes may interfere with binding of the siRNP endonuclease complex.

The sequence of the mRNA or cDNA is searched seeking the sequence AA(N19)TT (SEQ ID NO: 1 ). Sequences with approximately 50% G/C-content (30% to 70%) are used. If no suitable sequences are found, the search is extended to sequences AA(N21). The sequence of the sense siRNA corresponds to 5'-(N19)dTdT-3' or N21, respectively. In the latter case, the 3' end of the sense siRNA is converted to dTdT. The rationale for this sequence conversion is to generate a symmetric duplex with respect to the sequence composition of the sense and antisense 3' overhangs. It is believed that symmetric 3' overhangs help to ensure that the siRNPs are formed with approximately equal ratios of sense and antisense target RNA-cleaving siRNPs. The modification of the overhang of the sense sequence of the siRNA duplex is not expected to affect targeted mRNA recognition, as the antisense siRNA strand glides target recognition.

If the target mRNA does not contain a suitable AA(N21) sequence, it is recommended to search for NA(N21) The sequence of the sense and antisense strand may still be synthesized as 5' (N19)TT as the sequence of the 3' most nucleotide of the antisense siRNA does not appear to contribute to specificity.

It is further recommended to search the selected siRNA sequence against EST libraries in appropriate databases (e.g., NCBI BLAST database search) to ensure that only one gene is targeted.

At least one siRNA duplex is used. Although siRNA silencing appears to be extremely effective by selecting a single target in the mRNA, it is preferable to design and employ two independent siRNA duplexes to control for specificity of the silencing effect. Studies on the specificity of target recognition by siRNA duplexes indicate that a single point mutation located in the paired region of an siRNA duplex is sufficient to abolish target mRNA degradation.

The appropriately designed siRNAs are either obtained from commercial sources (such as Dharmacon Research, Lafayette, Colo.; Xergon, Huntsville, Ala.; Ambion, Austin, Tex.) or chemically synthesized used appropriately protected ribonucleoside phosphoramidites and a conventional DNA/RNA synthesizer according to standard protocols. The RNA oligonucleotides are fusser 2' deprotected, desalted and the two strands annealed, according to manufacturer's specifications or conventional protocols, depending on how the siRNAs are obtained. All handling steps are conducted under strict sterile, RNase-free conditions.

In certain embodiments, the nucleic acid based therapeutic agent is a nucleotide-associated protein. Exemplary nucleotide-associate proteins include, but are not limited to, various bacterial nucleoid-associated proteins, neuron-specific RNA binding proteins and their homologues in other species.

In certain embodiments, the biotinylated compositions comprise a therapeutic agent in addition to the nucleic acid based therapeutic agent. A "therapeutic agent" is any compound capable of preventing the establishment or growth (systemic or local) of a tumor or infection. Examples include drugs (e.g. antibiotics, anti-virals, antifungals), toxins (e.g. ricin), radionuclides (e.g. I-131, Re-186, Re-188, Y-90, Bi-212, At-211, Sr-89, Ho-166, Sm-153, Cu-67 and Cu-64), hormone antagonists (e.g. tamoxifen), heavy metal complexes (e.g. cisplatin), oligonucleotides (e.g. antisense nucleotides). Preferred therapeutic agents are drugs (e.g. antibiotics, anti-virals, antifungals), toxins (e.g. ricin), radionuclides (e.g. I-131, Re-186, Re-188, Y-90, Bi-212, At-211, Sr-89, Ho-166, Sm-153, Cu-67 and Cu-64), hormone antagonists (e.g. tamoxifen), heavy metal complexes (e.g. cisplatin), oligonucleotides (e.g. antisense oligonucleotides that bind to a target nucleic acid sequence (e.g. mRNA sequence)), chemotherapeutic nucleotides, peptides, non-specific (non-antibody) proteins (e.g. sugar oligomers), boron containing compound (e.g. carborane), photodynamic agents (e.g. rhodamine 123), enediynes (e.g. calicheamicins, esperamicins, dynemicin, neocarzinostatin chromophore, and kedarcidin chromophore) and transcription based pharmaceuticals. In a preferred embodiment for treating or preventing the establishment or growth of a tumor, the therapeutic agent is a radionuclide, toxin, hormone antagonist, heavy metal complex, oligonucleotide, chemotherapeutic nucleotide, peptide, non-specific (non-antibody) protein, a boron compound or an enediyne. In a preferred embodiment for treating or preventing the establishment or growth of a bacterial infection, the therapeutic agent is an antibiotic, radionuclide or oligonucleotide. In a preferred embodiment for treating or preventing the establishment or growth of a viral infection, the therapeutic agent is an antiviral compound, radionuclide or oligonucleotide. In a preferred embodiment for treating or preventing the establishment or growth of a fungal infection, the therapeutic agent is an antifungal compound radionuclide or oligonucleotide.

In certain embodiments, the therapeutic agent is capable of preventing the establishment of preventing the establishment or growth (systemic or local) of a tumor or infection.

A wide variety of antineoplastic agents may be used in conjunction with the biotinylated siRNA compositions for treating neoplastic diseases. Such antineoplastic agents can be categorized as: antibiotic agents, antimetabolic agents, plant derived agents, and biologic agents.

Antibiotic agents are a group of anticancer drugs that are produced in a manner similar to antibiotics by a modification of natural products. Examples of antibiotic agents include, but are not limited to, anthracyclines (e.g., doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and form an activated complex, which then binds to bases of DNA, causing strand scissions and cell death. Such a combination therapy may have therapeutic synergistic effects on cancer and reduce sides affects associated with these chemotherapeutic agents.

Other forms of antibodies include monoclonal antibodies. Monoclonal antibodies against tumor are antibodies elicited against antigens expressed by tumors, preferably tumor-specific antigens. Examples of monoclonal antibodies for cancer therapy include, but are not limited to, HERCEPTIN.®. (Trastruzumab), RITUXAN.®. (Rituximab), PANOREX.®. (edrecolomab), ZEVALIN.®. (ibritumomab yiuxetan), MYLOTARGT.®. (gemtuzumab ozogamicin), and CAMPATH.®. (alemtuzumab).

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Such a combination therapy may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), water soluble or insoluble camptothecin (e.g., 20(S)-camptothecin, 9-nitro-camptothecin, 9-nitro-camptothecin, and topotecan), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Camptothecin is believed to be a potent inhibitor of the nuclear enzyme DNA topoisomerase I (topo-I), which is responsible for "relaxation" of supercoiled double-stranded DNA by creating single-stranded breaks through which another DNA strand can pass during transcription. Topo-I reseals the break allowing DNA replication to occur. Inhibition of topo-I leads to the formation of stable DNA-topoisomerase complexes, with eventual formation of irreversible double-stranded DNA breaks, leading to apoptosis and/or other forms of cell death. Podophyllotoxins such as etoposide are believed to interfere with DNA synthesis by interacting with topoisomerase II, leading to DNA strand scission. Such a combination therapy may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a DNA methylation inhibitor, a histone deacetylase inhibitor and the biologic agent may have therapeutic synergistic effects on cancer, enhance the patient's immune responses to tumorigenic signals, and reduce potential sides affects associated with this biologic agent.

Cytokines possess profound immunomodulatory activity. Some cytokines such as interleukin-2 (IL-2, aldesleukin) and interferon-.alpha. (IFN-.alpha.) demonstrate antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with a DNA methylation inhibitor include, but are not limited to, interleukin 2 (IL-2), and interleukin 4 (IL-4), interleukin 12 (IL-12).

Interferon-.alpha. includes more than 23 related subtypes with overlapping activities, all of the IFN-.alpha. subtypes within the scope of the present invention. IFN-.alpha. has demonstrated activity against many solid and hematologic malignancies, the later appearing to be particularly sensitive. Examples of interferons that may be used in conjunction with a DNA methylation inhibitor include, but are not limited to, interferon-.alpha., interferon-.beta. (fibroblast interferon) and interferon-.gamma. (fibroblast interferon).

Other cytokines that may be used in conjunction with a DNA methylation inhibitor include those cytokines that exert profound effects on hematopoiesis and immune functions. Examples of such cytokines include, but are not limited to erythropoietin (epoietin-.alpha.), granulocyte-CSF (filgrastin), and granulocyte, macrophage-CSF (sargramostim). These cytokines may be used in conjunction with a DNA methylation inhibitor to reduce chemotherapy-induced myelopoietic toxicity.

Immuno-modulating agents other than cytokines may also be used in conjunction with a DNA methylation inhibitor to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

In certain embodiments, a diagnostic agent is covalently bound to the scaffold. The term diagnostic agent refers to a composition capable of generating a detectable image upon binding with a target, for example, a fluorescent moiety, a chromophore, a radionuclide or a metal atom. In certain embodiments, the diagnostic agent contains a radionuclide such as In-111, Tc-99m, I-123, I-125 F-18, Ga-67, or Ga-68. The diagnostic agent may be visualized using Positron Emission Tomography (PET) or Single Photon Emission Tomography (SPECT). In other embodiments, the diagnostic agent is an unpaired spin atom or free radical (e.g. Fe or Gd) or contrast agent (e.g. chelated (DTPA) manganese) for Magnetic Resonance Imaging (MRI). Additional diagnostic agents for Magnetic Resonance Imaging and fluorescent imaging are described in the discussion below under the sections Contrast Agents and Fluorescent Imaging.

In certain embodiments, said metal atom is selected to give the complex superior properties as a MRI contrast agent. In certain embodiments, said metal atom is In-111, Tc-99m, I-123, I-125 F-18, Ga-67, or Ga-68. In certain embodiments, the metal atom is selected to give the complex superior properties as a cancer treatment drug. In a preferred embodiment, the metal atom is $^{90}Y$, $^{99m}Tc$, $^{188}Re$, $^{32}P$, $^{166}Ho$, $^{109}Pd$, $^{140}La$, $^{153}$Sm, $^{165}$Dy, or $^{169}$Er. In a more preferred embodiment, the metal atom is $Gd^{3+}$, $Mn^{2+}$, $Fe^{3+}$, $Cr^{3+}$, dysprosium, holmium, or erbium.

In certain embodiments, a targeting moiety is covalently bound to the scaffold. Exemplary targeting moieties include lipids, antibodies, lectins, ligands, sugars, steroids, hormones, nutrients, and proteins. In certain embodiment, the targeting moiety is amino glycoside. In other embodiments, the targeting moiety is a lipophilic molecule.

Methods of the Invention

One aspect of the present invention relates to a method of treating disease in a mammal, comprising the step of:

administering to said mammal a therapeutically effective amount of a biotinylated composition of the invention, e.g. the compositions depicted in FIGS. 1-4.

In certain embodiments, the present invention relates to the aforementioned method, wherein said disease is a bacterial infection, viral infection, or cancer.

In certain embodiments, the present invention relates to the aforementioned method, wherein said disease is cancer.

In certain embodiments, the present invention relates to the aforementioned method, wherein said mammal is a human.

In certain embodiments, said compound comprises at least two biotin moieties. In a preferred embodiment, said compound comprises siRNA. In certain embodiments, said compound comprises a therapeutic agent and a nucleic acid based therapeutic agent (such as siRNA). In a preferred embodiment, the therapeutic agent comprises a radionuclide, antibiotic, antiviral, or antifungal compound. In a preferred embodiment, the therapeutic agent comprises a radionuclide.

A preferred embodiment of the method for the treatment of cancer using the administration of siRNA for modulating the expression of particular genes according to the present invention includes the selection of a gene to be targeted for silencing, by degradation of its corresponding mRNA, such that expression of that gene is inhibited. Genes appropriate for use include those known to be involved in cell growth and proliferation such as proliferation promoting factors, including cell cycle genes, a myriad of which are known (see Vogelstein, B, and Kinzler, K. W., The Genetic Basis of Human Cancer McGraw Hill, 2002 for examples). In a preferred embodiment of the method of the present invention the gene for fer is chosen for targeting as illustrated below in the examples. Alternate genes include those for cell cycle control genes such as cdks and cyclins as non-limiting examples.

The method further includes the step of selecting a target sequence in the target mRNA and design of the siRNA duplexes for the target mRNA. Target sequence selection and siRNA duplex design is based on the guidelines of Tuschl et al., as have become standard in the art (Tuschl, T., P. D. Zamore, R. Lehmann, D. P. Bartel and P. A Sharp Genes Dev 13: 3191-3197 (1999); The siRNA user guide [http://www.mpibpc.gwdg.de/abteilu-ngen/100/105/sima.html]; Elbashir S M, Harborth J, Weber K, Tuschl T. Methods February; 26(2):199-213, (2002); Technical Bulletin #003-Revision B, Dharmacon Research, Inc. Lafayette, Colo., 2002).

Hematologic disorders include abnormal growth of blood cells that can lead to dysplastic changes in blood cells and hematological malignancies such as various leukemias. Examples of hematological disorders include, but are not limited to, acute myeloid leukemia, acute promyelocytic leukemia, acute lymphoblastic leukemia, chronic myelogenous leukemia, the myelodysplastic syndromes, and sickle cell anemia.

Examples of cancers include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas. Examples of lymphomas include, for example, small lymphocytic lymphoma, follicular lymphoma, large B-cell lymphoma, mantle-cell lymphoma, and Burkitt lymphoma.

Another aspect of the present invention relates generally to a method generating a magnetic resonance image of a subject, comprising the steps of administering to a subject in need of magnetic resonance imaging a biotinylated composition of the invention comprising a diagnostic agent, and generating a magnetic resonance image. In certain embodiments, said compound comprises at least two biotin groups. In certain embodiments, said diagnostic agent comprises $Gd^{3+}$, $Mn^{2+}$, $Fe^{3+}$, or $Cr^{3+}$.

In certain embodiments, the present invention relates to the aforementioned method, wherein said subject is a human.

Yet another aspect of the present invention relates generally to a method generating a fluorescent image of a cell, comprising the steps of administering to a cell a biotinylated composition of the invention, and generating a fluorescent image of the cell.

Additional diagnostic agents for magnetic resonance imaging and fluorescent imaging are described in the discussion below under the sections Contrast Agents and Fluorescent Imaging.

Pharmaceutical Compositions

In another aspect, the present invention provides pharmaceutically acceptable compositions which comprise a therapeutically-effective amount of one or more of the biotinylated compositions described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H.

Freedman and CO., San Francisco, U.S.A., 1969 or "Livestock Feeds and Feeding" O and B books, Corvallis, Ore., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Cyclodextrins

Cyclodextrins are cyclic oligosaccharides, consisting of 6, 7 or 8 glucose units, designated by the Greek letter .alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a composition of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween.®. and Pluronic.®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Contrast Agents

Clinical imaging technology plays a significant role in diagnosis of injuries and disease processes. Many parts of the human body can now be examined using a variety of diagnostic imaging techniques. Radiography has long been used to image body parts through which externally generated x-rays are transmitted. Computerized axial tomography (CAT) provides cross-sectional x-ray images of a plane of the body. Specific tissues or organs may be targeted in positron emission tomography (PET), single photon emission computed tomography (SPECT), and gamma scintigraphy. In PET, SPECT, and gamma scintigraphy, radiopharmaceutical agents capable of being sequestered (concentrated) to some degree in the target tissue or organ are internally administered to the patient, and images are generated by detecting the radioactive emissions from the concentrated radiopharmaceutical agent. Some of the radiopharmaceutical agents currently used for imaging include nuclides such as $^{201}$Tl, $^{99m}$Tc, $^{133}$Xe, and the like; chelates of nuclides; radiolabeled metabolic agents such as $^{11}$C-deoxy-D-glucose, $^{18}$F-2-fluorodeoxy-D-glucose, [1-$^{11}$C]- and [$^{123}$I]-β-methyl fatty acid analogs, $^{13}$N-ammonia, and the like; infarct avid agents such as $^{99m}$Tc-tetracycline, $^{99m}$Tc-pyrophosphate, $^{203}$Hg-mercurials, $^{67}$Ga-citrate, and the like; and radiolabeled ligands, proteins, peptides, and monoclonal antibodies. Whole cells such as erythrocytes, platelets, leukocytes, and other cells may also be labeled with a radionuclide and function as radiopharmaceutical agents.

D. R. Elmaleh, et al. [(1984) Proc. Natl. Acad. Sci. USA 81, 918-921] disclosed the agent, $^{99m}$Tc-labeled Ap$_4$ A ($^{99m}$Tc-Ap$_4$ A), used to image tumors implanted in rats. Chelatation of $^{99m}$Tc to Ap$_4$ A in this study yielded a mixture, in which $^{99m}$Tc was conjugated to the Ap$_4$ A-dinucleotide and which also may have contained unchelated $^{99m}$Tc. This study was based on the premise that some human tumor cells are permeable to exogenous ATP and ADP, and that these cells incorporate the intact nucleotides in intracellular pools in contrast to normal cells. Ap$_4$ A was shown to permeate into hepatoma cells but not into a number of untransformed mammalian cell lines. In addition to accumulating in implanted tumors, $^{99m}$Tc-Ap$_4$A in the 1984 study also accumulated in kidney, liver, bone, muscle, and lung.

The amount and type of clinical information that can be derived from PET, SPECT, and gamma scintigraphic images is related in part to the ability to concentrate the radiopharmaceutical agent in the target tissue or organ. Although many radiopharmaceuticals are available for clinical use, the resolution of the image generated may be limited depending on various factors. The resolution of a particular imaging agent for imaging diseased or injured tissue depends in part on the affinity of the radiopharmaceutical for the site of injury or disease as compared to its affinity for surrounding healthy tissue.

In MRI the contrast in the images generated may be enhanced by introducing into the zone being imaged an agent generally referred to as a contrast agent, which affects the spin reequilibration characteristics of the nuclei (the "imaging nuclei" which generally are protons and more specially water protons) which are responsible for the resonance signals from which the images are generated. The enhancement obtained with the use of contrast agents enables particular organs or tissues to be visualized more clearly by increasing or by decreasing the signal level of the particular organ or tissue relative to that of its surroundings. Contrast agents raising the signal level of the target site relative to that of its surroundings are termed "positive" contrast agents whilst those lowering the signal level relative to surroundings are termed "negative" contrast agents. The majority of materials now being proposed as MRI contrast media achieve a contrast effect because they contain paramagnetic, superparamagnetic or ferromagnetic species.

For ferromagnetic and superparamagnetic contrast agents, which are negative MRI contrast agents, the enhanced image contrast derives primarily from the reduction in the spin reequilibration coefficient known as $T_2$ or as the spin-spin relaxation time, a reduction arising from the effect on the imaging nuclei of the fields generated by the ferromagnetic or superparamagnetic particles.

Paramagnetic contrast agents on the other hand may be either positive or negative MRI contrast agents. The effect of paramagnetic substances on magnetic resonance signal intensities is dependent on many factors, the most important of which are the concentration of the paramagnetic substance at the imaged site, the nature of the paramagnetic substance itself, and the pulse sequence and magnetic field strength used in the imaging routine. Generally, however, paramagnetic contrast agents are positive MRI contrast agents at low concentrations where their $T_1$ lowering effect dominates and negative MRI contrast agents at higher concentrations where their $T_2$ lowering effect is dominant. In either event, the relaxation time reduction results from the effect on the imaging nuclei of the magnetic fields generated by the paramagnetic centers.

The use of paramagnetic, ferromagnetic, and superparamagnetic materials as MRI contrast agents has been widely advocated and broad ranges of suitable materials have been suggested in the literature. For example Lauterbur and others have suggested the use of manganese salts and other paramagnetic inorganic salts and complexes (see Lauterbur et al. in "Frontiers of Biological Energetics", volume 1, pages 752-759, Academic Press (1978), Lauterbur in Phil. Trans. R. Soc. Lond. B289: 483-487 (1980) and Doyle et al. in J. Comput. Assist. Tomogr. 5(2): 295-296 (1981)). Runge et al. have suggested the use of particulate gadolinium oxalate (see for example U.S. Pat. No. 4,615,879 and Radiology 147(3): 789-791 (1983)), Schering A G have suggested the use of paramagnetic metal chelates, for example of aminopolycarboxylic acids such as nitrilotriacetic acid (NTA), N,N,N',N'-ethylenediaminetetraacetic acid (EDTA), N-hydroxyethyl-N,N',N'-ethylenediaminetriacetic acid (HEDTA), N,N,N',—N",N"-diethylenetriaminepentaacetic acid (DTPA), and 1,4,7,10-tetraazacyclododecanetetraacetic acid (DOTA) (see for example EP-A-71564, EP-A-130934, DE-A-3401052 and U.S. Pat. No. 4,639,365), and Nycomed A S have suggested the use of paramagnetic metal chelates of iminodiacetic acids (see EP-A-165728). Besides paramagnetic metals, paramagnetic stable free radicals have also been suggested for use as positive MRI contrast agents (see for example EP-A-133674).

Other paramagnetic MRI contrast agents are suggested or reviewed in, for example, EP-A-136812, EP-A-185899, EP-A-186947, EP-A-292689, EP-A-230893, EP-A-232751, EP-A-255471, WO85/05554, WO86/01112, WO87/01594, WO87/02893, U.S. Pat. No. 4,639,365, U.S. Pat. No. 4,687,659, U.S. Pat. No. 4,687,658, AJR 141: 1209-1215 (1983), Sem. Nucl. Med. 13: 364 (1983), Radiology 147: 781 (1983), J. Nucl. Med. 25: 506 (1984), WO89/00557 and International Patent Application No. PCT/EP89/00078.

Ferromagnetic (a term used herein to cover both ferrimagnetic and ferromagnetic materials) and superparamagnetic MRI contrast agents, for example sub-domain sized magnetic iron oxide particles either free or enclosed within or bound to a particle of a non-magnetic matrix material such as a polysaccharide, are disclosed by Schroder and Salford in WO85/02772, by Nycomed A S in WO85/04330, by Widder in U.S. Pat. No. 4,675,173, by Schering A G in DE-A-3443252 and by Advanced Magnetics Inc in WO88/00060.

Intravenous administration, at separate times, of the positive contrast agent Gd DTPA-dimeglumine (which following such administration rapidly distributes extracellularly) and of superparamagnetic ferrite particles was proposed by Weissleder et al. in AJR 150: 561-566 (1988) for imaging of liver cancers and by Carvlin et al. Society for Magnetic Resonance Imaging, 5th Annual Meeting, San Antonio, 1987, for studying renal blood flow. Carvlin and Weissleder's work on this topic is reported further in Proc. SPIE-Int.Soc.Opt.Eng. (1988) 914 Medical Imaging II, Pages 10-19 and AJR 150 115-120 (1988), respectively.

Fluorescence Imaging

Fluorescence is emitted when a fluorophore interacts with an incident photon (excitation). Absorption of the photon causes an electron in the fluorophore to rise from its ground state to a higher energy level. Then, the electron reverts to its original level, releasing a photon (fluorescence emission) whose wavelength depends upon the amount of energy that is released during reversion. A given fluorophore may emit at single or multiple wavelengths (creating an emission spectrum), as electrons drop from various orbitals to their ground states. The emission spectrum is constant for each species of fluorophore. Imaging finds many uses in fluorescence. As examples, consider the following: (1) An imaging system tuned to a specific emission spectrum can be used to localize a fluorophore. For example, cells expressing green fluorescent protein can be imaged and counted. (2) Changes in the fluorophore molecule (such as binding of fura-2 to Ca++) will lead to alterations in the emission spectrum. An imaging system can be used to measure these spectral changes, as an indication of changes in the environment of the fluorophore. (3) By measuring the intensity of fluorescence, an imaging system can estimate the concentration of a fluorescently tagged molecule. A common example of this is in the use of fluorescent microarrays for gene expression analyses.

Localization: Monochrome and Multispectral Fluorescence Imaging

In the simplest case (monochrome fluorescence imaging), a single fluorophore is used to mark a single molecular species. For example, glial fibrillary acidic protein (GFAP) labeled with fluorescein isothiocyanate (FITC) can be used to visualize regions of repair following CNS trauma. Similarly, a specific chromosomal DNA location can be shown by fluorescence in situ hybridization.

Multispectral fluorescence imaging demonstrates multiple molecular species in the same image. Each discrete fluorescent tag is visualized as a different color. For example, we might show Cy3 (green) and Cy5 (red), with the regions of overlap shown as mixtures of colors (e.g. red and green overlap shown as yellow). MCID® and AIS handle multispectral fluorescence in two ways.

For the best quality, each fluorophore is visualized independently, under optimal conditions. For example, discrete images of FITC and rhodamine fluorescence are created. The Image Fusion function then combines the two images into a single color image that shows inter-relationships among the tagged tissue components (Figure). This method yields the best image quality, for three reasons. First, high resolution, very sensitive cooled cameras can be used. Second, the fluorescence optics (e.g. excitation and emission filters) may be optimally tuned for each wavelength. Third, one has flexible control over the contribution of each discrete image to the final fused image.

For the most convenient operation, multiple fluorophores are visualized simultaneously. In this case, the optics provide simultaneous multispectral excitation and discrete emission wavelengths for each fluorophore. A color camera is used to image the multicolored specimen. As standard color cameras are not sufficiently sensitive to visualize fluorescence emission, an integrating color camera is used.

Quantification: Changes in Fluorophore Environment

Changes in pH, binding of the fluorophore to specific ions, and many other environmental factors can lead to an alteration in the emission spectrum of a fluorophore. Measurements of such changes were traditionally performed in cuvettes. However, various methods have been developed that allow imaging systems to be perform similar measurements at the cellular and subcellular levels. MCID includes dedicated functions for the quantification of changes in fluorophore environment.

Features in Fluorescence Imaging Systems

Typical fluorescence measurements include area and proportional area, number of fluorescent targets, and fluorescence intensity. The spatial measurements are quite straightforward, and are performed more or less well by most image analyzers. In contrast, intensity measurements can be rather tricky because fluorescence fades, and good calibration standards are difficult to create. MCID's proven competence in quantitative intensity measurement lets you concentrate on the specimens, not on the weaknesses of the measurement instrument. Importantly, standard video cameras are not well suited to fluorescence applications, and a specialized low-light camera is usually necessary. However, a broad variety of integrating cameras available for use with MCID and AIS.

Fluorescence Imaging Components

Intensified CCDs (ICCDs) consist of a video camera mated to an image intensifier. The intensifier amplifies incident illumination by an adjustable factor. ICCDs are fast, in that they take a short time image relatively dim specimens. Their main drawbacks are grainy images at high amplification, poor rendition of contrast in fine details, and a severely limited intra-scene dynamic range. That is, ICCDs cannot see both bright and dim material within one image (typical dynamic range of about 40:1). ICCDs are best suited to dynamic fluorescence imaging, where their ability to provide images quickly is a critical advantage. For most purposes, GEN IV intensifier is recommended, which exhibits much better image quality than other variants. Various ICCD cameras are available, but we recommend the Roper Instruments video ICCD with GEN IV intensifier, integrating CCD camera, and control unit. This is about as sensitive as a single-stage ICCD gets, and has the added benefit of being very flexible. For extremely dim specimens, multistage intensifiers are available, and are often used in photon counting applications. In our opinion, the trials of working with a multistage ICCD are significant, and it is preferable to use the Black Ice cryogenic integrating cameras when ultimate sensitivity is required.

Integrating cameras are like film. They accumulate incident illumination over time. In general, integrating cameras provide better image quality and broader dynamic range than intensified cameras. MCID and AIS support a variety of integrating cameras. Integrating video cameras are low in cost and suitable for moderately bright specimens such as many immunolabeled cells. For bright specimens, the camera does not need to be cooled. For dimmer specimens, chilled (above 0 degrees C.) or cooled (below 0 degrees C.) integrating video cameras are still cost-effective. However, do not expect any video camera to function with demanding specimens. Integrating video technology sacrifices sensitivity and dynamic range (limited to 8-10 bits) in exchange for low cost.

The next step above video is a family of moderately priced integrating cameras (e.g. the Roper Sensys or Hamamatsu 4742), which use high resolution CCDs that can be operated in integration mode. Typically, these cameras are chilled to above-zero temperatures, and make fine images with fluorescent specimens.

For more difficult specimens, scientific-grade, cooled cameras can be used. The exact definition of a "scientific grade" camera varies but, generally, these devices use full-coverage CCDs, high precision digitizers (>12 bits), and deep cooling. The most advanced of these cameras use special, high-sensitivity CCDs and cryogenic cooling (cool below −100 C). The Black Ice camera incorporates every technical advantage that known, to yield performance that is absolutely state-of-the-art. Unfortunately, Black Ice technology is costly, but there are many scientific-grade cameras that are reasonably priced and yield excellent performance.

The Imaging System

A single video frame (made in 1/30 sec) from an intensified camera will be very grainy. The quality of the low-light image is improved by real-time averaging. Therefore, ICCD cameras may be interfaced to any imaging system capable of rapid frame averaging. It is useful if the imaging system can also construct ratios and perform fluorescence background subtraction in real time.

Integrating cameras can present more of a challenge to the imaging system. Efficient use of an integrating camera presents the following requirements: (1) Integrated camera and software: Although MCID/AIS can use images from any camera (by importing TIFF files), it is convenient if the image analysis software also controls the various exposure and data transfer parameters of the camera. Doing image acquisition within dedicated camera software and image analysis in a separate package is very tedious. (2) Accept high precision data: The imaging system must accept and calibrate to data at high bit densities (integrating cameras supply data at 8-16 bits). (3) Fast interface: The imaging system should include a fast interface to the integrating camera. The best cameras come with a dedicated connection (e.g. RS422) to the imaging system interface board, or with their own interface card. Acquiring images via a SCSI or other slow connection is cheaper and easier for the manufacturer to implement, but really degrades imaging throughput.

MCID includes fast and efficient control of integrating cameras, and can be calibrated to high bit densities. AIS is more limited in the variety of cameras it supports, but retains the ability to use high bit densities and the direct control of supported integrating cameras.

Dynamic Fluorescence Imaging

MCID includes dedicated software for dynamic fluorescence as part of the standard image analysis package. This has two major benefits. a) The system that performs quantitative autoradiography, morphometry, and fluorescence densitometry can also perform ratiometric measurements without any additional software expense. b) Dynamic fluorescence imaging does not have to be learned as a discrete program. Rather, analysis, archiving, annotation, enhancement, and other operations are all easily performed on sequences of fluorescence images, using familiar MCID functions. MCID will acquire very large numbers of closely-spaced images directly into the computer. This on-line dynamic imaging is available with all of MCID's supported cameras, including ICCDs and integrating cameras.

Ratiometric Imaging

Ratiometric imaging takes advantage of the spectral shifts displayed when fluorescent dyes bind to their target ions. MCID supports various types of ratiometric imaging, including fura-2 imaging of calcium and BCECF imaging of pH.

The calcium chelator, fura-2, is used to measure cytosolic free Ca++ concentrations. The saturating calcium form of fura-2 has a maximum absorbance at about 335 NM. The calcium free form absorbs maximally at about 362 NM. The ratio (usually 340:380) of intensities of fluorescence changes by about an order of magnitude between saturated and calcium-free solutions. Thus, a relative brightening of the 340 image reflects an increase in the proportion of Fura-2 bound to Ca++.

Discrete 340 and 380 nm images are formed of cells incubated or injected with fura-2. The 340 and 380 nm images are corrected by the appropriate background, and a ratio image is formed. The ratio of 340 nm to 380 nm is passed through a simple equation (see below) to arrive at an estimate of Ca++ concentration.

Rmin is the ratio (340:380) of fluorescence intensity, formed at minimum Ca++ concentration. Rmax is the ratio (340:380) formed at saturating Ca++ concentration. F0/Fs is the ratio (380 nm) of fluorescence intensity at minimum and saturated Ca++ concentration. KD is the equilibrium dissociation constant for Ca++ and fura-2, usually stated as about 225 (Grynkiewicz, Poenie and Tsien, 1985; Williams and Fay, 1990). Each laboratory should calibrate the fura-2 technique under its own conditions. The ratio image can be displayed by using spectral color to represent calcium concentration. The ratio can also be displayed by modulating color and intensity independently. In this case, intensity reflects the intensity of the original component images (essentially equivalent to the confidence of the ratio at that point in the image), and color reflects calcium concentration.

A popular indicator dye for intracellular pH is BCECF (Rink, Tsien and Pozzan, 1982; Bright et al., 1987). BCECF fluoresces strongly at visible wavelengths, with an excitation peak at 503 nm and an emission peak at 525 nm. Both peaks are pH-dependent, being quenched by acidification and enhanced by more alkaline environments. At 436-439 nm, however, fluorescence is independent of pH. Therefore, a ratio can be constructed between pH-dependent and pH-independent BCECF images. In theory, this ratio will reflect pH independent of irrelevant influences such as dye concentration, illumination intensity, etc. A filter set for pH measurement with BCECF includes excitation filters at 440 and 495 nm, a 515 nm dichroic mirror and an emission filter at 535 nm. Backgrounds are acquired at 440 and 495 nm. All the procedures are as for Ca++ imaging. Ratios are passed through the following equation:

$$pH = pK + \log(R - R\max)(R\max - R)$$

R is the normalized 495/440 nm fluorescence ratio, obtained as a ratio of the mean intensity value over any portion of the image, at each wavelength, at a pH of 7.0. One starts with a value of 7.17 for pK, and suggest that one calculate values appropriate for your conditions. BCECF is most commonly calibrated by using the K+/H+ ionophore, nigericin, to expose cells to known internal pHs (Thomas, et al., 1979).

To correct background fluorescence, one creates a ratio image from two excitation images (we will use 340 and 380 nm as examples). MCID offers three modes for correcting the excitation images prior to ratio formation: a) Subtractive: removal of background fluorescence and intensifier or camera offset. Background values for each of 340 and 380 nm images are entered. These background values are automatically subtracted from the 340 and 380 images before ratios are calculated. This is a simple, one-step correction, in that the same background error is applied over the entire field of view. b) Proportional: correction of shading error. Two independent, pixel-by-pixel shading corrections are applied; one for each excitation image. A blank field (the shading field) is acquired at each excitation. In both shading fields, each pixel's error is expressed as a proportion. Subsequent excitation images are corrected by the appropriate proportions before calculation of any ratios. c) Subtractive+proportional: Both subtractive and proportional shading correction can be used.

Flexible Excitation Conditions

A ratio image is calculated from images taken at two excitation wavelengths. In the simplest case, we take a single image at each excitation wavelength and then construct a ratio. However, any sequence of images may be acquired and processed before construction of a ratio. For example, one might construct a final image from a sequence of 340/380 alterations. This can avoid differential bleaching at one wavelength. One can also specify skipping of discrete excitation conditions. For example, a sequence of 20 timed ratios are taken, using 380 nm images taken every second. However, 340 nm images are taken only every three seconds.

Reading and Graphing Data from Multiple Ratio Images

Data from any number of timed ratios may be read simultaneously. By placing a sample tool onto a phase or DIC image, onto any excitation image, or onto any ratio image, MCID will report data across an entire experiment. The report will include any or all of:

gray level value at excitation 1 and 2
ratio
Ca++ concentration or other measurement Photometer Mode In some cases one does not need images. Rather one wishes to generate a single image, define regions of interest on that image and then have the system read ratios from those regions over time. It is as if one were using the imaging system as a photometer with multiple view windows. MCID allows any number of "photometer windows" to be placed on the image, and then reads the density values of these windows to construct the ratio.

Photometer mode generates a set of ratio and Ca++ concentration values across time. Any period of time may be used, and any number of regions may be read, as there are no memory storage requirements for the photometer data. The numerical values may be graphed, either during or following the acquisition process.

Adjusting the Two Excitation Wavelengths

Ideal ratiometric imaging requires that all images be acquired at near-equal intensities, well within the linear range of camera operation. Integrating cameras offer an elegant solution to the problem of balancing intensities. One can simply adjust the integration time differently for each excitation. This is quickly and easily done, using MCID's ratiometric functions.

There is more of a problem with ICCDs. ICCD brightness could be balanced by changing intensifier amplification (under computer control) for each wavelength. This is convenient but dangerous, unless intensifier response has been demonstrated to be linear across a range of amplification factors. Another option is to decrease fluorescence intensity at the brighter wavelength by using an ND filter mounted prior to the excitation filter. Various attenuation filters (e.g. 25%, 50%, 75%) may be mounted at different positions in the filter wheel, or in a second wheel. This option requires some fiddling with the filter wheel, but allows intensifier amplification to be maintained at a constant level.

Single Excitation, Single Emission

Single excitation, single emission procedures are much simpler than ratiometry. All that is necessary is that we acquire images at timed intervals, and then measure fluorescence intensity values from those images. Changes in fluor location escence intensity or fluor location (e.g. internalization of a receptor labeled with GFP) can be tracked. Changes in intensity are generally qualitative. That is, one can state that a change in fluorescence emission occurs, but one cannot quantify the change in terms of ionic concentrations.

An example of a single emission procedure is use of the Ca++ indicator fluo-3. It is excited at 503-506 nm, in the visible portion of the spectrum. Fluo-3 has a weaker affinity for Ca++ (KD about 400 nm) than do fura-2 or indo-1, permitting measurement of lower Ca++ concentrations. It also exhibits very marked changes in fluorescence intensity (about 4 decades) with Ca++ binding. Compare this with the tenfold change in fluorescence intensity exhibited by fura-2. MCID's single emission option is similar in use to fura-2 imaging, though there is only one excitation wavelength. As filter wheel changes are not required, rather short inter-image intervals are possible.

Kits

The present invention provides kits for treating and imaging various diseases, for example, cancers. For example, a kit may comprise one or more biotinylated composition as described above and optionally instructions for their use. In still other embodiments, the invention provides kits comprising one or more pharmaceutical or diagnostic compositions and/or one or more devices for accomplishing administration of such compositions. For example, a subject kit may comprise a pharmaceutical or diagnostic composition and catheter for accomplishing direct intraarterial injection of the composition into a cancerous tumor.

Exemplification

The invention now being generally described, it will be more readily understood by reference to the following examples, which are included merely for purposes of illustration of certain aspects and embodiments of the present invention, and are not intended to limit the invention.

Example 1

Biotinylation Promotes Cellular Uptake of siRNA

Biotinylation of siRNA compositions enables delivery into tumor cells. PC-3 human prostate carcinoma cells were used as a model system to compare the delivery of unlabeled, Cy3-labeled and biotin-labeled siRNAs into tumor cells. In these experiments Lamin A/C was used as the target gene, due to its demonstrated use in published siRNA studies.

Figure 5:
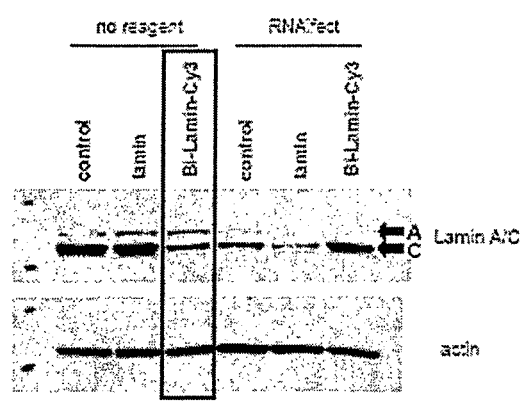
FIG. 5 depicts Western blots of PC-3 cells treated with non-binding control, Lamin, or Biotin-Lamin-Cy3 labeled siRNAs in biotin-containing culture media. Upper blot, lamin A/C antibody. Lower blot, actin antibody as loading control. The highlighted box indicates a lane with decreased lamin A/C expression following Biotin-lamin-Cy3 siRNA treatment.

FIG. 5 shows the delivery of control siRNA, unlabeled lamin siRNA and lamin siRNA labeled with a 5'Biotin and 3'Cy3 label on the sense strand of the synthetic siRNA. PC-3 cells were treated with these siRNAs both in the absence of delivery reagent and in the presence of RNAifect (Qiagen) lipid-based delivery reagent, used as a positive control for siRNA efficacy. In the absence of delivery reagent the level of Lamin A/C was reduced by the biotinylated lamin siRNA, relative to control. No reduction in lamin A/C protein levels was seen using unlabeled lamin siRNA under the same conditions. This experiment was performed in biotin-containing culture media that would be expected to compete for biotin uptake.

Figure 6:
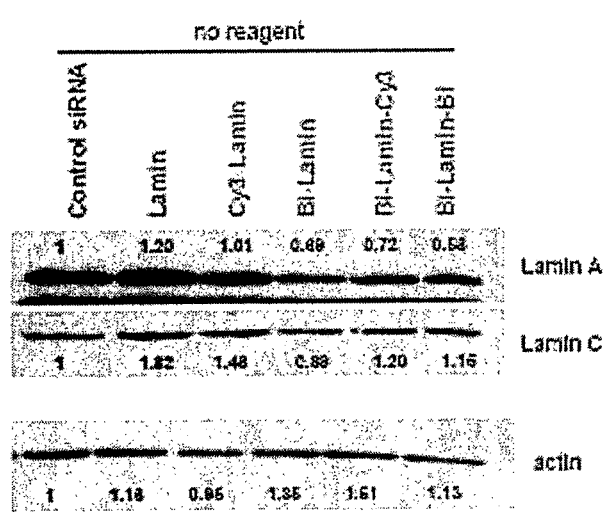
FIG. 6 depicts Western blots of PC-3 cells treated with lamin siRNAs in biotin-free culture media. The Western blots show lamin A (upper blot), lamin C (middle blot) and actin (lower blot). Quantitation of bands using Scion Image (NIH) indicates that Lamin A protein level significantly decreased in the presence of biotinylated lamin siRNAs, with 42-47% lamin A inhibition after correction for protein loading.

This experiment has also been repeated in biotin-free cell culture media, with additional labeled siRNA controls, as shown in FIG. 6. It should be noted that some background biotin would be available from the fetal bovine serum used to supplement the media. FIG. 6 shows that various biotin-labeled lamin siRNAs were capable of knocking down lamin expression, in the absence of any delivery reagent.

Figure 7:
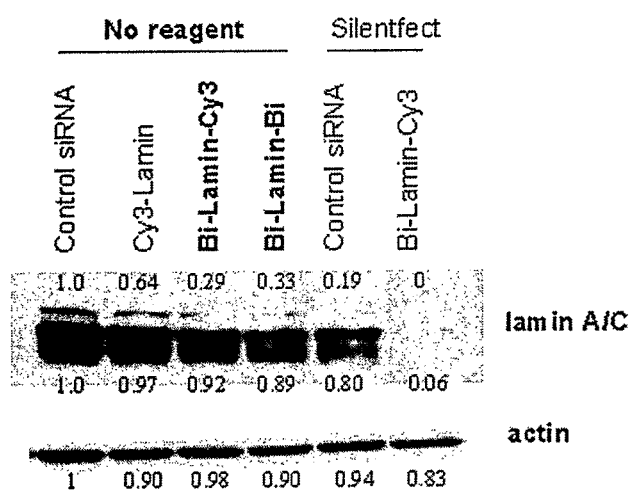
FIG. 7 depicts Western blots of PC-3MLN4 cells treated with labeled lamin siRNAs in biotin-free culture media. Upper blot, lamin A/C antibody. Lower blot, actin antibody as loading control. Bold type indicates biotinylated siRNA treatments in the absence of delivery reagent. Quantitation of bands using Scion Image (NIH) indicates that Lamin A protein level decreased in the presence of biotinylated lamin siRNAs. Lamin C change was not significant under these conditions. As positive controls, biotinylated lamin siRNA complexed to Silentfect lipid delivery agent was used, as shown in lanes 5 and 6.

These experiments have also been repeated using a more aggressive tumor cell line, PC-3MLN4. This is a metastatic subline of PC-3 prostate carcinoma cells. As shown in FIG. 7, biotinylated siRNAs were able to decease specific protein expression in the absence of delivery reagent in these cells. Biotinylated siRNAs decreased lamin A protein expression by 72-74%, after inhibition was corrected for protein loading.

In summary, this data indicates that biotinylated siRNAs are taken up by tumor cells in the absence of delivery reagent, and act functionally to silence gene expression.

Example 2

Targeting V12-K-Ras Using Biotinylated siRNA

Ras genes have been observed to be mutated in 85% of human pancreatic cancers and 40% of colon cancers. The human v-Ki-ras2 gene accession # NM_004985) is therefore a compelling target for siRNA therapy. In Brummelkamp et al, (2002) Cancer Cell 2:243-247, retrovirally produced siRNA was used to stably knock down V12-K-ras in pancreatic cancer cells, decreasing tumor formation.

Brummelkamp, et al. targeted the following sequence:

```
                                              (SEQ ID NO: 2)
    5'GTT GGA GCT GTT GGC GTA G
```

The Brummelkamp, et al. V12-K-ras siRNA sequence may be biotinylated as described above to produce any of a variety of biotinylated compositions of the invention The siRNA sequence used by Brummelkamp, et al. may further be optimized as follows:

```
Target Sequence (sense):
                                (SEQ ID NO: 3)
    5'GAG CTG TTG GCG TAG GCA A
                                (SEQ ID NO: 4)
    (GAG CUG UUG GCG TAG GCA A)
```

In the wild-type sequence, T=G. The optimized V12-K-ras siRNA sequence may be biotinylated as described above to produce any of a variety of biotinylated compositions of the invention. The various V12-K-ras biotinylated siRNA compositions may be tested using the human colon model cell line Capan-1.

References

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Fire et al. (1998) Nature 391, 806-811; Elbashir, S. M., Lendeckel, W., & Tuschl, T. (2001). Genes Dev. 15, 188-200; Parrish, S., Fleenor, J., Xu, S., Mello, C., & Fire, A. (2000). Mol. Cell. 6, 1077-1087; Nykanen, A., Haley, B., & Zamore, P. D. (2001). Cell 107, 309-321; Elbashir, S. M., Martinez, J., Patkaniowska, A., Lendeckel, W., & Tuschl, T. (2001). EMBO J. 20, 6877-6888; Hammond, S. M., Bernstein, E., Beach, D., & Hannon, G. J. (2000). Nature (London) 404, 293-296; Zamore, P. D., Tuschl, T., Sharp, P. A., & Bartel, D. P. (2000). Cell 101, 25-33; Bass, B. L. (2001). Nature (London) 411, 428-429; Yang, D., Lu, H., & Erickson, J. W. (2000). Curr. Biol. 10, 1191-1200; Boutla, A., Delidakis, C., Livadaras, I., Tsagris, M., & Tabler, M. (2001). Curr. Biol. 11, 1776-1780; Sijen, T., Fleenor, J., Simmer, F., Thijssen, K. L., Parrish, S., Timmons, L., Plasterk, R. H., & Fire, A. (2001). Cell 107, 465-476; Lipardi, C., Wei, Q., & Paterson, B. M. (2001). Cell 107, 297-307; Elbashir, S. M., Harborth, J., Lendeckel, W., Yalcin, A., Weber, K., & Tuschl, T. (2001). Nature (London) 411, 494-498; Billy, E., Brondani, V., Zhang, H., Muller, U., & Filipowicz, W. (2001). Proc. Natl. Acad. Sci. USA 98, 14428-14433; Yang, S., Tutton, S., Pierce, E., & Yoon, K. (2001). Mol. Cell. Biol. 21, 7807-7816; Paddison, P. J., Caudy, A. A., & Hannon, G. J. (2002). Proc. Natl. Acad. Sci. USA 99, 1443-1448; Robertson, H. D. & Mathews, M. B. (1996). Biochimie 78, 909-914; Harborth, J., Elbashir, S. M., Bechert, K., Tuschl, T., & Weber, K. (2001). J. Cell Sci. 114, 4557-4565; Hutvagner, G., McLachlan, J., Pasquinelli, A. E., Balint, E., Tuschl, T., & Zamore, P. D. (2001). Science 293, 834-838; Grosshans, H. & Slack, F. J. (2002). J. Cell Biol. 156, 17-22; Song, E., Lee, S. K., Wang, J., Ince, N., Ouyang, N., Min, J., Chen, J., Shankar, P. and Lieberman, J. (2003) Nature Med. 9, 347-351; Davidson, B. L. and Paulson, H. L. (2004) Lancet Neurol. 3, 145-149; Tolentino, M. J., Brucker, A. J., Fosnot, J., Ying, G. S., Wu, I. H., Malik, G., Wan, S. and Reich, S. J. (2004) Retina 24, 132-138; Layzer, J. M., McCaffrey, A. P., Tanner, A. K., Huang, Z., Kay, M. A. and Sullenger, B. A. (2004) RNA 10, 766-771; Filleur, S., Courtin, A., Ait-Si-Ali, S., Guglielmi, J., Merle, C., Harel-Bellan, A., Clezardin, P. and Cabon, F. (2003) Cancer Res., 63, 3919-3922; Krieg, A. M. (2002) Annu. Rev. Immunol. 20, 709-760.

Equivalents

The present invention provides, among other things, biotinylated compositions comprising a nucleic acid based therapeutic agent. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:

1. A composition consisting of a polymer scaffold conjugated to (i) one, two, three, or four biotin moieties, and (ii) one or two therapeutic double-stranded RNA molecules having a sense strand and an antisense strand, wherein the sense or the antisense strand is conjugated to one or two biotin moieties.

2. The composition of claim 1, wherein said therapeutic double-stranded RNA molecule is siRNA.

3. The composition of claim 1, wherein the sense strand is conjugated to two biotin moieties.

4. The composition of claim 1, wherein the antisense strand is conjugated to two biotin moieties.

5. The composition of claim 1, wherein the sense strand and the antisense strand are each conjugated to two biotin moieties.

6. A pharmaceutical composition, comprising a composition of claim 1 or claim 2, and a pharmaceutically acceptable excipient.

7. The composition of claim 1, wherein the sense strand is conjugated to one biotin moiety; and the antisense strand is conjugated to one biotin moiety.

8. The composition of claim 1, wherein the sense strand is conjugated to two biotin moieties; and the antisense strand is conjugated to one biotin moiety.

9. The composition of claim 1, wherein the antisense strand is conjugated to two biotin moieties; and the sense strand is conjugated to one biotin moiety.

10. A method of delivering a therapeutic double-stranded RNA molecule to a cell or tissue comprising the step of
    contacting the cell or tissue with a composition of claim 1.

11. A method of treating a disease in a mammal in need thereof, comprising the step of
    administering to said mammal a therapeutically effective amount of a composition of claim 1.

12. The method of claim 11, wherein said disease is a bacterial infection, viral infection, or cancer.

* * * * *

UNITED STATES PATENT AND TRADEMARK OFFICE
CERTIFICATE OF CORRECTION

PATENT NO. : 8,669,236 B2
APPLICATION NO. : 11/914332
DATED : March 11, 2014
INVENTOR(S) : David R. Elmaleh et al.

It is certified that error appears in the above-identified patent and that said Letters Patent is hereby corrected as shown below:

In the Specification

At Column 1, Line number 11, immediately before "BACKGROUND OF THE INVENTION," please insert:
--GOVERNMENT SUPPORT
This invention was made with government support under CA104973 awarded by the National Institutes of Health. The government has certain rights in the invention.--

Signed and Sealed this
Ninth Day of May, 2023

Katherine Kelly Vidal
*Director of the United States Patent and Trademark Office*